United States Patent
Li et al.

(10) Patent No.: US 9,562,884 B2
(45) Date of Patent: Feb. 7, 2017

(54) METHOD FOR MANUFACTURING $NO_2$ GAS SENSOR FOR DETECTION AT ROOM TEMPERATURE

(71) Applicant: INSTITUTE OF MICROELECTRONICS, CHINESE ACADEMY OF SCIENCES, Beijing (CN)

(72) Inventors: Dongmei Li, Beijing (CN); Shuang Zhan, Beijing (CN); Shengfa Liang, Beijing (CN); Xin Chen, Beijing (CN); Changqing Xie, Beijing (CN); Ming Liu, Beijing (CN)

(73) Assignee: Institute of Microelectronics, Chinese Academy of Sciences, Beijing (CN)

( * ) Notice: Subject to any disclaimer, the term of this patent is extended or adjusted under 35 U.S.C. 154(b) by 0 days.

(21) Appl. No.: 14/896,342

(22) PCT Filed: Jun. 5, 2013

(86) PCT No.: PCT/CN2013/076761
§ 371 (c)(1),
(2) Date: Dec. 4, 2015

(87) PCT Pub. No.: WO2014/194484
PCT Pub. Date: Dec. 11, 2014

(65) Prior Publication Data
US 2016/0123944 A1    May 5, 2016

(51) Int. Cl.
*C03C 15/00* (2006.01)
*G01N 33/00* (2006.01)
(Continued)

(52) U.S. Cl.
CPC .......... *G01N 33/0036* (2013.01); *G01N 27/00* (2013.01); *G01N 27/12* (2013.01); *G01N 33/0037* (2013.01)

(58) Field of Classification Search
CPC .... G01N 27/00; G01N 27/12; G01N 33/0036; G01N 33/0037; G01N 33/0006
(Continued)

(56) References Cited

U.S. PATENT DOCUMENTS 5,948,587 A * 9/1999 Kawabe ................ G03F 7/0236
                                              430/165
8,020,456 B2 * 9/2011 Liu ........................ B82Y 10/00
                                              73/862.621
(Continued)

FOREIGN PATENT DOCUMENTS

CN         101824603 A     9/2010
CN         102661981 A     9/2012
(Continued)

*Primary Examiner* — Lan Vinh
(74) *Attorney, Agent, or Firm* — Christensen Fonder P.A.

(57) ABSTRACT

A method for manufacturing an $NO_2$ gas sensor for detection at room temperature comprises: manufacturing a metal electrode on a surface of a flexible substrate; manufacturing an $SWCNTs/SnO_2$ sensitive film; and bonding the $SWCNTs/SnO_2$ sensitive film with a portion of the surface of the flexible substrate with the metal electrode, so as to form the $NO_2$ gas sensor for detection at room temperature. The present disclosure solves the problems of the poor adhesion between the sensitive material and the flexible substrate, and a non-uniform distribution, and achieves the purposes of secure bonding between the sensitive material and the flexible substrate, and uniform distribution.

7 Claims, 3 Drawing Sheets

(51) Int. Cl.
*G01N 27/00* (2006.01)
*G01N 27/12* (2006.01)

(58) Field of Classification Search
USPC .......................... 216/13, 17, 20, 33, 35, 41
See application file for complete search history.

(56) References Cited

U.S. PATENT DOCUMENTS

| | | | |
|---|---|---|---|
| 2010/0310792 A1* | 12/2010 | Wei | B82Y 30/00 427/600 |
| 2011/0147715 A1* | 6/2011 | Rogers | B82Y 10/00 257/24 |
| 2012/0006102 A1* | 1/2012 | Bryant | G01N 27/127 73/61.43 |
| 2012/0080319 A1* | 4/2012 | Myung | B82Y 15/00 205/159 |
| 2012/0224327 A1* | 9/2012 | Kabir | B01J 23/755 361/713 |

FOREIGN PATENT DOCUMENTS

| | | |
|---|---|---|
| JP | 2006-162431 A | 6/2006 |
| WO | WO 2011/146128 A1 | 11/2011 |

\* cited by examiner

METHOD FOR MANUFACTURING NO₂ GAS SENSOR FOR DETECTION AT ROOM TEMPERATURE

CROSS-REFERENCE TO RELATED APPLICATION(S)

This application is a U.S. national phase application of PCT Application No. PCT/CN2013/076761 filed on Jun. 5, 2013, entitled "MANUFACTURING METHOD OF NO₂ GAS SENSOR FOR DETECTION AT ROOM TEMPERATURE". This PCT Application is incorporated herein by reference in its entirety.

TECHNICAL FIELD

The present disclosure relates to the field of gas sensor technology, and in particular, to a method for manufacturing an NO₂ gas sensor for detection at room temperature.

BACKGROUND

With the development of science and technology, sensors are applied widely, and it is imperative to manufacture sensors which are portable and inexpensive and can be manufactured at a large scale. Flexible substrate-based gas sensors essentially improve a lot of problems due to many advantages such as flexibility thereof or the like. Thereby, the flexible substrate-based gas sensors have a broader application prospect.

NO₂ belongs to typical atmospheric pollutants, and primarily comes from burning of fossil fuel and automobile exhaust pollution. NO₂ is one of industrial pollutants which cause problems such as acid rain, photochemical smog or the like, and causes respiratory disease as it easily reacts with hydrocarbon in the sunshine, which seriously threatens the health and survival of human beings. With the rapid development of industries, people pay more and more attention to monitoring of NO₂. Researches on NO₂ gas sensors are a hotspot at home and abroad all the time. In order to improve the sensitivity characteristics of the sensors, people have put much effort on selection and modification of material. With the rapid development of Internet of Things, sensors with a portable design and low power consumption are widely concerned. Therefore, it is a very important task to manufacture a flexible NO₂ gas sensor for detection at room temperature.

A conventional method for manufacturing a flexible NO₂ gas sensor for room temperature is to directly deposit a sensitive film on a surface of a flexible substrate. In the process of manufacturing a sensor, hygroscopic treatment is firstly performed on the substrate, and then sensitive material is deposited on a surface of the substrate using dip-coating, dispensing or self-growing method. The sensitive film manufactured in this way has a non-uniform thickness, and poor adhesion with the substrate.

SUMMARY

Technical Problems to be Solved

The purpose of the present discourse is to provide a method for manufacturing an NO₂ gas sensor for detection at room temperature, thereby solving the problems of the poor adhesion between the sensitive material and the flexible substrate, and a non-uniform distribution, and achieving the purposes of secure bonding between the sensitive material and the flexible substrate, and uniform distribution.

Technical Solutions

In order to achieve the above purposes, the present disclosure provides a method for manufacturing an NO₂ gas sensor for detection at room temperature, comprising:
manufacturing a metal electrode on a surface of a flexible substrate;
manufacturing an SWCNTs/SnO₂ sensitive film; and
bonding the SWCNTs/SnO₂ sensitive film with a portion of the surface of the flexible substrate with the metal electrode to form the NO₂ gas sensor for detection at room temperature.

In the above solution, manufacturing the metal electrode on the surface of the flexible substrate comprises:
cleaning the flexible substrate, coating photoresist on the surface of the flexible substrate, and photoetching the photoresist to remove photoresist formed at the metal electrode on the surface of the flexible substrate to form an electrode pattern on the surface of the flexible substrate; then depositing a Cr film and an Au film in turn on the flexible substrate with the electrode pattern using electron beam evaporation; and finally stripping the photoresist and the Cr film and Au film on the photoresist, to form the flexible substrate having the metal electrode on the surface thereof.

In the above solution, the flexible substrate comprises PI, PET or PEN.

In the above solution, the photoresist coated on the surface of the flexible substrate is positive photoresist comprising 9920 or 3220.

In the above solution, manufacturing an SWCNTs/SnO₂ sensitive film comprises:
disproportionating CO under a high pressure to generate a carbon nano tube, mixing the carbon nano tube with an organic metal solution of 2-ethylhexanoate and performing ultrasonic oscillation on them for 1.5 to 2.5 hours to obtain homogeneous mixed suspension liquid; then coating the suspension liquid on the SiO₂ base with spinning, dispensing, dip-coating or screen printing and drying to evaporate solvent in a suspension liquid coating; then calcining the SiO₂ base for which the solvent in the suspension liquid coating is evaporated to obtain an SWCNTs/SnO₂ sensitive film bonded with the SiO₂ base; and finally etching to remove the SiO₂ base with HF acid to separate the SWCNTs/SnO₂ sensitive film from the SiO₂ base so as to obtain the SWCNTs/SnO₂ sensitive film.

In the above solution, in calcining the SiO₂ base for which the solvent in the suspension liquid coating is evaporated to obtain the SWCNTs/SnO₂ sensitive film bonded with the SiO₂ base, a reaction equation when the 2-ethylhexanoate is calcined is as follows:

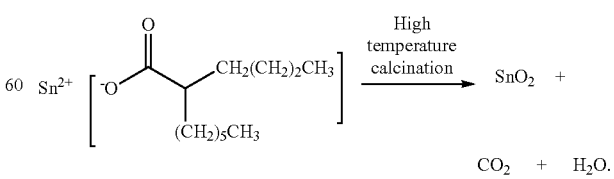

In the above solution, the high temperature calcination is performed at a temperature within 300-1000° C.

In the above solution, bonding the SWCNTs/SnO$_2$ sensitive film with the portion of the surface of the flexible substrate with the metal electrode to form the NO$_2$ gas sensor for detection at room temperature comprises:

coating a conductive silver paste layer on the portion of the surface of the flexible substrate with the metal electrode, and bonding the SWCNTs/SnO$_2$ sensitive film with the portion of the surface of the flexible substrate with the metal electrode using the conductive silver paste to form the NO$_2$ gas sensor for detection at room temperature.

Beneficial Effects

The method for manufacturing an NO$_2$ gas sensor for detection at room temperature according to the present disclosure avoids an operation on the flexible substrate at a high temperature in the process of manufacturing the sensitive film by bonding the material of the sensitive film with the flexible substrate in an indirect manner. This method comprises firstly coating an SWCNTs/SnO$_2$ sensitive film on an SiO$_2$ base, and then etching to remove the SiO$_2$ base using HF acid, to separate the SWCNTs/SnO$_2$ sensitive film from the SiO$_2$ base; and coating a conductive silver paste layer on an electrode surface of the flexible substrate to bond the sensitive film with the flexible substrate. This method overcomes the problems of a non-uniform distribution of the sensitive material and the poor adhesion between the sensitive material and the flexible substrate for the sensitive film which is manufactured with the conventional method using dip-coating, dispensing or self-growing, and achieves a more uniform distribution of the sensitive material on the surface of the flexible substrate and enhances the adhesion between the sensitive material and the flexible substrate by directly reacting on the surface of the SiO$_2$ base to generate sensitive material and bonding the material of the sensitive film with the flexible substrate in an indirect manner.

BRIEF DESCRIPTION OF THE DRAWINGS

For better illustrating the content of the present disclosure, the present disclosure will be described in detail below in conjunction with accompanying drawings and examples, wherein in the accompanying drawings:

FIG. 2-1 is a diagram of a flexible substrate;

FIG. 2-2 is a diagram of coating photoresist on the flexible substrate and forming an electrode pattern on the flexible substrate;

FIG. 2-3 is a diagram after depositing a Cr film and an Au film on the flexible substrate with an electrode pattern;

FIG. 2-4 is a diagram of stripping the photoresist and the Cr film and the Au film thereon to obtain a flexible substrate with a metal electrode;

FIG. 2-5 is a diagram of an SiO$_2$ base;

FIG. 2-6 is a diagram of forming a sensitive film on the SiO$_2$ base;

FIG. 2-7 is a diagram of an SWCNTs/SnO$_2$ sensitive film which is left after etching to remove a lower SiO$_2$ base with HF acid;

FIG. 2-8 is a diagram of coating a conductive silver paste layer on a portion of the surface of the flexible substrate with the metal electrode; and FIG. 2-9 is a diagram of bonding the SWCNTs/SnO$_2$ sensitive film with the portion of the surface of the flexible substrate with the metal electrode using the conductive silver paste.

DETAILED DESCRIPTION

In order to make the purposes, technical solutions, and advantages of the present disclosure more clear and obvious, the present disclosure will be further described in detail below in conjunction with specific embodiments and with reference to accompanying drawings.

The technical idea of the present disclosure is as follows: disproportionating CO under a high pressure to generate a carbon nano tube, mixing the carbon nano tube with an organic metal solution of 2-ethylhexanoate and performing ultrasonic oscillation on them for 1.5 to 2.5 hours (preferably, 2 hours) to obtain homogeneous mixed suspension liquid; then coating the suspension liquid on an SiO$_2$ base in a manner such as spinning, dispensing, dip-coating or screen printing and drying to evaporate solvent in a suspension liquid coating; then calcining the SiO$_2$ base for which the solvent in the suspension liquid coating is evaporated for 0.5 to 4 hours to obtain a composite SWCNTs/SnO$_2$ sensitive film; etching to remove lower SiO$_2$ base with HF acid to separate the SWCNTs/SnO$_2$ sensitive film from the SiO$_2$ base; and coating a conductive silver paste layer on an electrode surface of the flexible substrate, and bonding the sensitive film with the flexible substrate to form a flexible NO$_2$ gas sensor for detection at room temperature.

Figure 1:
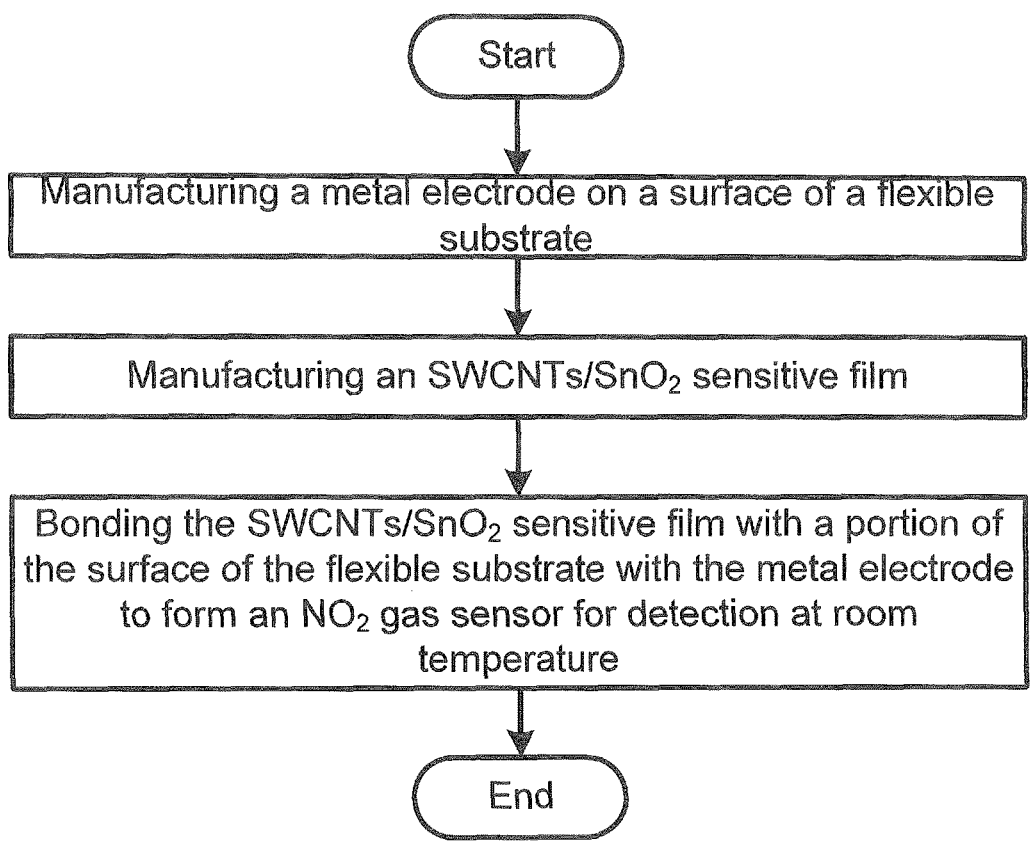
FIG. 1 is a flowchart of a method for manufacturing an NO$_2$ gas sensor for detection at room temperature according to the present disclosure.

As shown in FIG. 1, FIG. 1 is a flowchart of a method for manufacturing an NO$_2$ gas sensor for detection at room temperature according to the present disclosure. The method comprises the following steps.

In a first step, a metal electrode is manufactured on a surface of a flexible substrate.

Figures 1, 2:
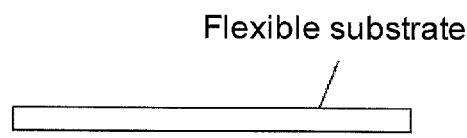
Figure 2:
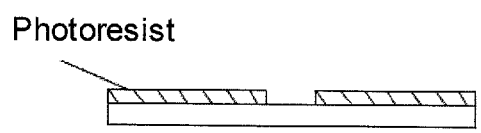
Figures 2, 3:
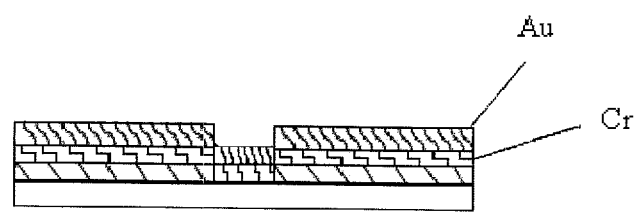
Figures 2, 3, 4:
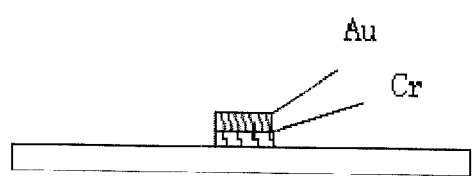
Figures 2, 3, 4, 5:
Figures 2, 3, 4, 5, 6:
Figures 2, 3, 4, 5, 6, 7:
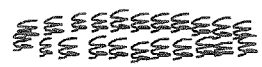
Figures 2, 3, 4, 5, 6, 7, 8:
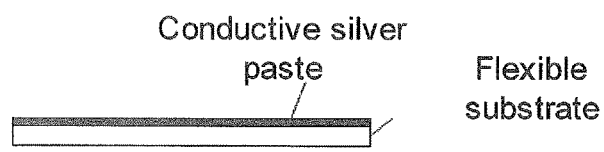
Figures 2, 3, 4, 5, 6, 7, 8, 9:
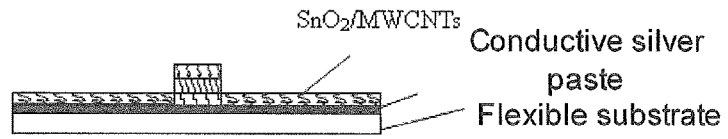

In this step, firstly the flexible substrate is cleaned, as shown in FIG. 2-1. The flexible substrate at least comprises PI, PET or PEN or the like, has advantages such as portability, a low price, and excellent flexibility or the like, and can extend the application prospect of the sensors. Then, as shown in FIG. 2-2, photoresist is coated on the flexible substrate. The photoresist used herein is positive photoresist comprising 9920, 3220 or the like. The photoresist is photoetched to remove photoresist formed at the metal electrode on the flexible substrate to form an electrode pattern on the flexible substrate. Then, as shown in FIG. 2-3, a Cr film and an Au film are deposited in turn on the flexible substrate with an electrode pattern using electron beam evaporation or other coating technology. Finally, as shown in FIG. 2-4, the photoresist and the Cr film and Au film on the photoresist are stripped, to form a flexible substrate with the metal electrode. Other coating technology is magnetic sputtering, CVD, spinning, screen printing or the like, with the purpose of depositing a uniform film on the surface of the substrate.

In a second step, an SWCNTs/SnO$_2$ sensitive film is manufactured.

In this step, CO is disproportionated under a high pressure to generate a carbon nano tube, the carbon nano tube is mixed with an organic metal solution of 2-ethylhexanoate and ultrasonic oscillation is performed on them for 1.5 to 2.5 hours (preferably, 2 hours) to obtain homogeneous mixed suspension liquid (this process is merely a mixing process, without chemical reaction). Then, the suspension liquid is coated on the SiO$_2$ base in a manner such as spinning, dispensing, dip-coating or screen printing. The SiO$_2$ base is shown in FIG. 2-5. Drying is performed to evaporate solvent in a suspension liquid coating, and then the $SiO_2$ base for which the solvent in the suspension liquid coating is evaporated is calcined for 0.5 to 4 hours at a temperature within 300° C.-1000° C. to obtain an $SWCNTs/SnO_2$ sensitive film bonded with the $SiO_2$ base, as shown in FIG. 2-6. Etching is performed with HF acid to remove a lower $SiO_2$ base to separate the $SWCNTs/SnO_2$ sensitive film from the $SiO_2$ base so as to obtain an $SWCNTs/SnO_2$ sensitive film, as shown in FIG. 2-7.

In the process of calcining the $SiO_2$ base for which the solvent in the suspension liquid coating is evaporated to obtain an $SWCNTs/SnO_2$ sensitive film bonded with the $SiO_2$ base, a reaction equation when the 2-ethylhexanoate is calcined to manufacture $SnO_2$ is as follows:

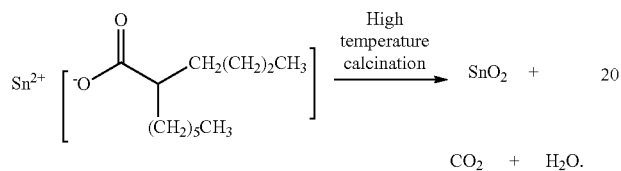

In a third step, the $SWCNTs/SnO_2$ sensitive film is bonded with a portion of the surface of the flexible substrate with the metal electrode to form an $NO_2$ gas sensor for detection at room temperature.

In this step, as shown in FIG. 2-8, a conductive silver paste layer is coated on the portion of the surface of the flexible substrate with the metal electrode. As shown in FIG. 2-9, the $SWCNTs/SnO_2$ sensitive film is bonded with the portion of the surface of the flexible substrate with the metal electrode using the conductive silver paste to obtain the $NO_2$ gas sensor for detection at room temperature. The $NO_2$ gas sensor can have better sensitivity for detecting $NO_2$ at room temperature.

It can be seen from the above embodiments that the method for manufacturing an $NO_2$ gas sensor for detection at room temperature according to the present disclosure avoids an operation on the flexible substrate at a high temperature in the process of manufacturing the sensitive film by bonding the material of the sensitive film with the flexible substrate in an indirect manner, overcomes the problems of a non-uniform distribution of the sensitive material and the poor adhesion between the sensitive material and the flexible substrate or the like for the sensitive film which is manufactured with the conventional method using dip-coating, dispensing or self-growing, and achieves a more uniform distribution of the sensitive material on the surface of the flexible substrate and enhances the adhesion between the sensitive material and the flexible substrate by directly reacting on the surface of the $SiO_2$ base to generate sensitive material and bonding the material of the sensitive film with the flexible substrate in an indirect manner.

The purposes, technical solutions and beneficial effects of the present disclosure are further described in detail in the specific embodiments described above. It should be understood that the above description is merely specific embodiments of the present disclosure, and is not intended to limit the present disclosure. Any amendment, equivalent substitution, improvement or the like, which is made within the spirit and principle of the present disclosure, should be included in the protection scope of the present disclosure.

We claim:

1. A method for manufacturing an $NO_2$ gas sensor for detection at room temperature, comprising:
   manufacturing a metal electrode on a surface of a flexible substrate;
   manufacturing an $SWCNTs/SnO_2$ sensitive film; and
   bonding the $SWCNTs/SnO_2$ sensitive film with a portion of the surface of the flexible substrate with the metal electrode to form the $NO_2$ gas sensor for detection at room temperature,
   wherein manufacturing the $SWCNTs/SnO_2$ sensitive film comprises:
   disproportionating CO under a high pressure to generate a carbon nano tube, mixing the carbon nano tube with an organic metal solution of 2-ethylhexanoate and performing ultrasonic oscillation for 1.5 to 2.5 hours to obtain a homogeneous mixed suspension liquid; then coating the suspension liquid on a $SiO_2$ base with spinning, dispensing, dip-coating or screen printing and drying to evaporate solvent in a suspension liquid coating; then calcining the $SiO_2$ base for which the solvent in the suspension liquid coating is evaporated to obtain the $SWCNTs/SnO_2$ sensitive film bonded with the $SiO_2$ base; and finally etching to remove the $SiO_2$ base with HF acid to separate the $SWCNTs/SnO_2$ sensitive film from the $SiO_2$ base so as to obtain the $SWCNTs/SnO_2$ sensitive film.

2. The method according to claim 1, wherein bonding the $SWCNTs/SnO_2$ sensitive film with the portion of the surface of the flexible substrate with the metal electrode to form the $NO_2$ gas sensor for detection at room temperature comprises:
   coating a conductive silver paste layer on the portion of the surface of the flexible substrate with the metal electrode, and bonding the $SWCNTs/SnO_2$ sensitive film with the portion of the surface of the flexible substrate with the metal electrode using the conductive silver paste to form the $NO_2$ gas sensor for detection at room temperature.

3. The method according to claim 1, wherein in calcining the $SiO_2$ base for which the solvent in the suspension liquid coating is evaporated to obtain the $SWCNTs/SnO_2$ sensitive film bonded with the $SiO_2$ base, a reaction equation when the 2-ethylhexanoate is calcined is as follows:

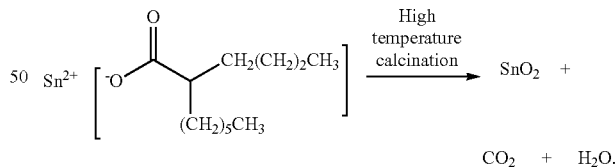

4. The method according to claim 3, wherein the high temperature calcination is performed at a temperature within 300-1000° C.

5. The method according to claim 1, wherein manufacturing the metal electrode on the surface of the flexible substrate comprises:
   cleaning the flexible substrate, coating photoresist on the surface of the flexible substrate, and photoetching the photoresist to remove photoresist formed at the metal electrode on the surface of the flexible substrate so as to form an electrode pattern on the surface of the flexible substrate; then depositing a Cr film and an Au film in turn on the flexible substrate with the electrode pattern using electron beam evaporation; and finally stripping the photoresist and the Cr film and Au film on the photoresist, to form the flexible substrate having the metal electrode on the surface thereof.

6. The method according to claim 5, wherein the flexible substrate comprises PI, PET or PEN.

7. The method according to claim 5, wherein the photoresist coated on the surface of the flexible substrate is positive photoresist comprising 9920 or 3220.

* * * * *